United States Patent [19]

Shepherd

[11] Patent Number: 5,264,539

[45] Date of Patent: Nov. 23, 1993

[54] THERMALLY STABLE OLIGOMERIC ULTRAVIOLET STABILIZERS

[75] Inventor: James P. Shepherd, Springfield, N.J.

[73] Assignee: Hoechst Celanese Corp., Somerville, N.J.

[21] Appl. No.: 866,160

[22] Filed: Apr. 9, 1992

[51] Int. Cl.$^5$ .................... C08G 69/44; C08G 63/44
[52] U.S. Cl. ................................ 528/272; 528/288; 528/289
[58] Field of Search .................. 528/272, 288, 289

[56] References Cited

U.S. PATENT DOCUMENTS

| | | | |
|---|---|---|---|
| 4,265,805 | 5/1981 | Thomas | 524/102 |
| 4,366,207 | 12/1982 | Anthony | 428/412 |
| 4,386,177 | 5/1983 | Loffelman | 524/100 |
| 4,439,564 | 3/1984 | Chasar | 524/101 |
| 4,455,401 | 6/1984 | Son et al. | 524/91 |
| 4,529,533 | 7/1985 | Chasar | 524/101 |
| 5,089,614 | 2/1992 | Lai | 544/71 |

Primary Examiner—John Kight, III
Assistant Examiner—T. Mosley
Attorney, Agent, or Firm—P. S. Kalyanaramau

[57] ABSTRACT

The invention discloses oligomeric compositions that have high thermal and uv stability as well as reactive end groups so that they may be reactively incorporated into polymer backbones when the polymers are prepared. The oligomeric moieties are capable of retaining their chemical structure intact at temperatures where the polymers are processed into articles, so that the finished articles contain the oligomeric moieties and possess good stability towards ultraviolet light. An example of such oligomer is illustrated by the following poly(aminoterephthalic acid).

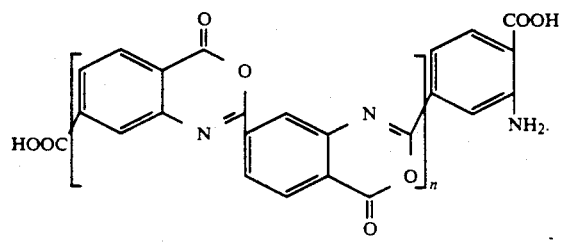

11 Claims, No Drawings

THERMALLY STABLE OLIGOMERIC ULTRAVIOLET STABILIZERS

The present application relates to oligomeric compositions that are useful as stabilizers for polymers against degradation by ultraviolet radiation. The compositions are especially useful for polymers which are processed at high temperatures. They can be incorporated into the backbone of the polymers to be processed, or used as blended additives during processing.

BACKGROUND OF THE INVENTION

In the last few decades, the production of polymers and plastics has been increasing rapidly. Among polymers, those that are processable into shapes such as films, fibers, and other objects have been in much commercial demand for various applications. Recent years have seen an increase in demand for polymers which have high temperature stability so that they can be processed at high temperatures with no degradation or chemical change, and the finished products may be used in high temperature applications such as, for example, those that are encountered in the electronics and aerospace industries.

Several uses for polymers are in outdoor applications where they are subjected to actions by light, heat, atmospheric oxygen and other environmental agents. Weathering conditions have always been an important problem in such applications. Ultraviolet radiation is especially a problem since it can not only cause degradation in the polymer on its own, but also cause a chemical change in the polymer which may consequently become vulnerable to attack by other environmental conditions. Thus, protection of polymers from ultraviolet radiation has been of interest for many years. A description of techniques to protect polymers from ultraviolet radiation is provided by J. F. Rabek, *Photostabilization of Polymers-Principles and Applications,* Elsevier Applied Science, New York, 1990.

Many approaches have been taken in the past to protect polymers from ultraviolet (uv) radiation. Generally, small molecules that are good uv absorbers are used as additives in the formulation. During the exposure, these additives absorb the uv radiation preferentially, thus preventing the radiation from reaching the polymer. For example, the Uvinul TM materials (from BASF Corporation, Chemicals Division, Parsippany, N.J.) and the Tinuvin TM additives (from Ciba Geigy Corporation, Additives Department, Hawthorne, N.Y.) are uv stabilizers that are commercially available for use with polymers. Such materials, however, have problems with thermal stability. Recently, several new polymers have come on the market which need to be or can be processed at high temperatures, for example, above 300° C. When additives such as those mentioned above are used as uv stabilizers (alternately referred to as photostabilizers) with such high temperature polymers which are then processed at high temperatures, the additives either thermally decompose or sublime away, leaving the polymer with no uv protection.

Polymeric stabilizers have been proposed to overcome this thermal instability problem. In such materials, the additive uv absorbing moieties are bound to polymer backbones. *Photostabilization of Polymers,* referred to above, describes several polymer-bound additives on pages 202-278. Polymer-bound stabilizers generally are used as additives to the polymers which are to be protected. These materials also have drawbacks. Some of them, even as part of polymer, may still be inherently thermally unstable. Another drawback is that depending on their molecular weights, some polymers may be limited in the amounts that can be added. They may also not stay as a homogeneously distributed part of the final product. Compatibility with the polymer to be protected may be yet another drawback.

Thus, there is a need for materials which can function as uv stabilizing agents that are stable under high temperature process conditions. It will be desirable if they can not only be used as blended additives to the polymer to be protected, but also as materials that can be incorporated into the backbone of the polymer that is to be protected. When incorporated into the backbone, the protecting moieties may stay as an integral, compatible part of the product at desired concentrations.

Accordingly, it is an object of this invention to provide oligomeric uv stabilizers that possess high thermal stability.

It is another object of this invention to provide oligomeric uv stabilizers that possess reactive functionalities so they may be incorporated into the backbone of polymers.

It is a further object of this invention to provide oligomeric uv stabilizers which can be used as compatible blended additives for polymers.

It is yet another objective of this invention to provide oligomeric uv stabilizers that possess high enough thermal stabilities to withstand high temperature processing of polymers to which they are added or in which they are incorporated in the backbone, so that the resulting finished product retains uv stability.

These and other objects of the present invention will become apparent to the skilled artisan upon a review of the following specification, and claims.

SUMMARY OF THE INVENTION

In one embodiment the present invention includes an oligomeric composition of matter which comprises, in its repeat units, moieties that absorb ultraviolet radiation. The repeat units generally number about 2-200, specifically 2-100, and typically 2-20. The moieties contain reactive functionalities which facilitate the incorporation of the moieties into a polymer backbone during the formation of the polymer. The moieties inherently possess sufficient thermal stability to withstand the processing conditions of the polymer in which they are incorporated. If and when the polymers are processed at high temperatures to finished products, the moieties are present in the finished products with their chemical structural integrity preserved so that the finished product stays protected against uv degradation. The term "high temperatures" refers to temperatures of about 300-350° C.

DESCRIPTION OF THE INVENTION

The present invention discloses oligomeric compositions that comprise, in their repeat units, moieties which possess ultraviolet stability as well as high thermal stability. The number of such repeat units in the oligomer is generally about 2-200, specifically about 2-100, and typically about 2-20. Such oligomers, when incorporated into polymers, offer uv stability to the resulting polymers. Incorporation may be achieved in many ways into the polymer compositions which are to be protected against ultraviolet radiation. For example, the oligomers may be blended with the polymer, or they may be reactively incorporated into the polymer. In the former method, an already formed polymer is physically blended with the oligomer in required amounts. In the latter case, the oligomer possesses reactive functionalities in its chemical formula; during the reaction to make the polymer the oligomer is included in requisite amounts and reacted, so that the finished polymeric composition may comprise the oligomeric moieties as intrinsic units in its backbone.

The uv stable moieties in the oligomer have the property of absorbing uv radiation. An example is the benzoxazin-4-one type moiety. Additionally, they must also possess sufficient thermal stability to withstand processing temperatures of over about 300° C. The term "sufficient thermal stability to withstand" refers to the capability to retain chemical structural integrity at such temperatures. Such moieties are particularly valuable when the incorporated polymers are processed at high temperatures. Then the processed polymer as well as the product obtained by processing of the polymer still retains the uv stable moieties that protect such polymer and product from uv radiation.

The invention may be illustrated by the oligomeric composition of Formula 1 which contains benzoxazin-4-one moieties:

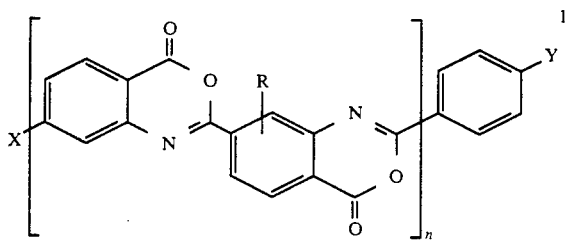

wherein R=H. an alkyl group containing up to about 12 carbons, a cycloalkyl containing up to about 8 carbons, an alkoxy group containing up to about 8 carbons, halide, or an aryl group containing up to about 10 carbons, X and Y are same or different and are selected from the group consisting of $NH_2$, NHR, COOH, and OH, with R referring to the same alkyl, cycloalkyl and aryl groups described above, and n is an integer between 2 and 200.

The oligomeric composition of Formula 1 possesses high temperature stability. The synthesis of the oligomer may be done in such a way as to fix the number n of the benzoxazin-4-one moieties repeat units in the chain, thus defining the molecular weight of the oligomer. Additionally, one may choose appropriate reactive end groups for X and Y in Formula 1, to be compatible with the nature of the polymer into which the oligomer is to be incorporated. Thus, for example, when the polymer is a polyester to be made from a diol and a diacid, X and Y may be both OH, or both $CO_2H$. If, on the other hand, the polyester is to be prepared by polymerizing a monomer that contains both an alcohol and an acid, either X or Y may be OH, and the other $CO_2H$ group.

The synthesis of an oligomer of the invention containing benzoxazin-4-one moieties and $NH_2$, and $CO_2H$ end groups may be illustrated as follows (see Scheme 1). The starting material for its preparation is aminoterephthalic acid (Formula 3). Compound 3 may be prepared by hydrolYsis of dimethyl aminoterephthlate (Formula 2, available from Aldrich Chemical Company, Milwaukee, Wis.).

SCHEME 1

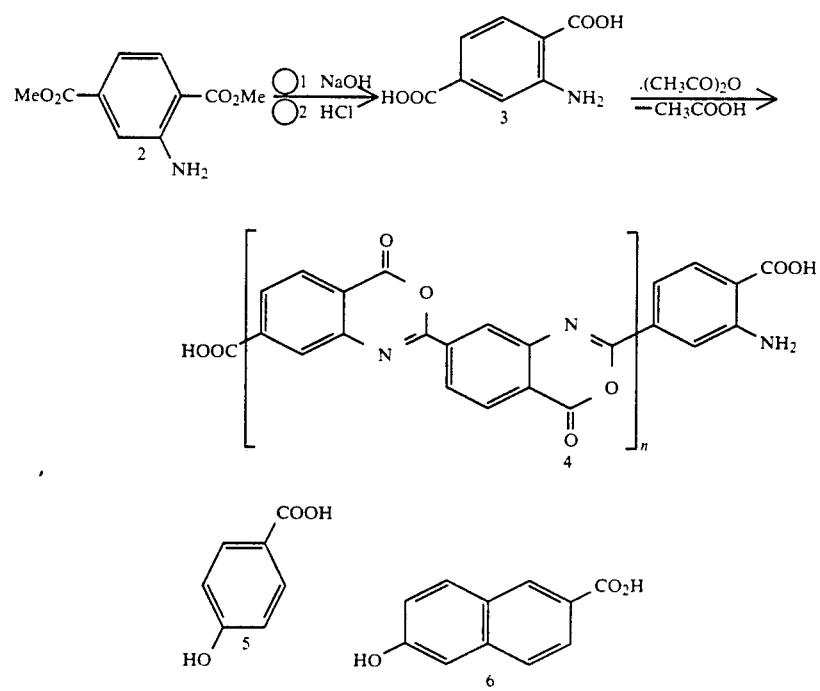

SCHEME 1

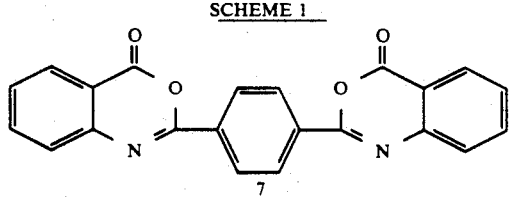

7

Thus, for example, compound 2 may be refluxed in aqueous NaOH solution, and then acidified to isolate the desired diacid 3. Compound 3 may be reacted in a suitable manner to cause condensation/dehydration to form the desired oligomeric compound 4. A convenient way is to take compound 3 in a suitable solvent such as, for example, acetic anhydride, along with a catalyst such as, for example, potassium acetate, and reflux while removing the water formed in the reaction. Crystals of the oligomer 4 that form in the reaction may then be filtered, dried, and analyzed by techniques known to those skilled in the art such as, for example, IR and NMR spectroscopy and the like. The thermal stability may be measured by customary techniques such as thermogravimetric analysis (TGA).

Incorporation of the oligomer 4 into a polyester may be illustrated as follows. Compound 4, 4-hydroxy benzoic acid (Formula 5), and 6-hydroxy-2-naphthoic acid (Formula 6) may be taken in a suitable vessel in a solvent such as, for example, acetic anhydride, along with a catalyst such as, for example, potassium acetate, and refluxed under suitable conditions, whereby the polyester with the oligomeric moiety incorporated is formed. The amount of compound 4 taken initially determines the amount of the oligomeric moiety present in the polyester. The formation of the polyester in the above reaction may be monitored by observing changes in the viscosity of the reaction mixture, as shown in a torque indicator in the reaction vessel. The reaction may be terminated when the torque reading reaches a desired level. Cooling of the reaction mixture generally results in the separation of the polymer which may be isolated and analyzed by customary techniques for polymer analysis. This polymer is generally good enough for processes such as, injection molding, spinning, and the like, to produce finished articles.

Instead of the incorporated polymer above, a blended polymer containing the oligomer of Formula 4 may be prepared, if so desired. For example, oligomer 4 may be blended with a polyester prepared from compounds 5 and 6 in a desired ratio, and the mixture may be run through an extruder to produce a blend that can then be used for processes such as injection molding, spinning, and the like, to make finished articles.

Polymers wherein the oligomeric stabilizers of the invention are incorporated in suitable amounts in the backbone generally have physical properties that are not significantly different from polymers without the stabilizers incorporated. The result is that the incorporated polymers may be processed under very similar conditions as the unincorporated polymers without significant change. Thus, for example, spinning behavior of the incorporated polymers is not significantly different from that of unincorporated polymers. Spinning of fibers from polymers containing oligomers of the invention may be illustrated as follows. A polyester with the oligomer incorporated in its backbone, such as, for example the one described earlier, may be ground into a fine powder and then compressed into rods. The rods may be placed in the heating block of a fiber extruder, melted, and then extruded through a suitable spinneret. Spin temperatures of, for example, 300° C., may be used. The spun filaments may then be quenched in air. They may then be heat treated in an oven, generally in the presence of nitrogen, at a suitable temperature. Since these filaments as well as the oligomeric moieties contained therein are thermally stable, heat treating at temperatures in excess of, for example, 250° C. are possible with no decomposition. The fibers may be tested for physical properties such as, for example, tensile strength, elongation, and tensile modulus, by conventional techniques. Physical properties of some of the polymers of the invention are described in Table I. In the Tables, polymer from Example 4 contains the oligomeric stabilizer incorporated into the polymer backbone. Polymer from Example 5 has a nonoligomeric aminoterephthalic acid moiety incorporated into the polymer backbone. Polymer from Example 3 is a control polymer with no stabilizer in it; it was made from compounds 5 and 6 by a process similar to that described above.

As noted earlier, polymers containing the oligomers of the invention are thermally stable enough to be processed at temperatures above 300° C. without degradation, whereas if a nonoligomeric small molecule stabilizer is used in place of the oligomer, degradation occurs. Thus, the nonoligomeric moiety, 2,2'-phenylene-bis-(4H-3,1-benzoxazin-4-one) (Formula 7) was prepared as described by D. J. Bain et al., *J. Chem. Society (C)*, 1593 (1968), and this nonoligomeric benzoxazin-4-one stabilizer compound was mixed with a polyester. In the Tables, polymer from Example 6 denotes such a blend. Attempts to spin fibers from this blended composition at temperatures above 300° C. resulted in sublimation and degradation of the stabilizer compound. In an attempt to compensate for this loss, the amount of the nonoligomeric benzoxazin-4-one moiety had to be substantially increased in the blend. Thus, for example, polymer from Example 6 in the Tables contains four times the benzoxazin-4-one units per molecule, as compared to the polymer from Example 4 (wherein the oligomeric functionality is chemically incorporated). Despite that increased amount of stabilizer, the overall properties of the blended polymer from Example 6 were significantly inferior to those of the polymer from Example 4.

The uv stability of the polymers containing the oligomeric stabilizers therein may be demonstrated by techniques such as, for example, weatherometer testing of the fibers made from spinning the polymers. The as-spun fibers, for example, may be placed, along with fibers made from the control polymer, in a weatherometer, and exposed to a uv source for several days, periodically measuring their physical properties that would show the decrease in fiber strength. Such data is presented in Tables II and III as well as in FIGS. 1 and 2.

They demonstrate the superior stability of polymers containing the oligomeric stabilizers of the invention.

EXAMPLES

In the following Examples, g refers to grams, ml to milliliters, ° C. refers to degrees Celsius, and ambient temperature to temperatures about 21°–29° C.

EXAMPLE 1: PREPARATION OF AMINOTEREPHTALIC ACID (FORMULA 3)

A representative preparation was done as follows: Dimethyl aminoterephthalate (5 g), cetyltrimethyl ammonium bromide catalyst (0.05 g) and aqueous NaOH solution (5%, 300 ml) were taken in a 500 ml round bottom flask, and heated to and held at about 60° C. for about 2 hours. The mixture was then cooled to about 15°–20° C., and acidified with concentrated HCl when the acid of Formula 3 separated as yellow crystals. This was filtered, washed with ice cold water, and dried (yield: 89%).

EXAMPLE 2: PREPARATION OF THE OLIGOMERIC STABILIZER, POLY(AMINOTEREPHTHALIC ACID), FORMULA 4

Aminoterephthalic acid from Example 1 (1.96 g), potassium acetate catalyst (0.01 g), and acetic anhydride (100 ml) were taken in a flask fitted with a Dean-Stark adapter carrying a condenser on top. The mixture was refluxed for about 8–10 hours, periodically (about every 1.5 hour) removing the acetic acid/anhydride mixture off. Fresh acetic anhydride was added to the flask periodically to replace the acetic anhydride lost. Then the brown solution was cooled and concentrated in a rotary evaporator. The oligomer of Formula 4 separated as brown crystals which were collected and recrystallized from an acetic acid: acetic anhydride (1:1 v/v) mixture (0.98 g, yield: 50%).

EXAMPLE 3: PREPARATION OF CONTROL POLYMER (CO 73/27) FROM COMPOUNDS 5 AND 6 WITHOUT THE OLIGOMERIC STABILIZER

4-Hydroxybenzoic acid (4.38 moles), 6-hydroxy-2-naphthoic acid (1.62 mole), and potassium acetate (0.12 mmole) were charged to a 2 liter 3-necked flask ("slim Jim") equipped with Vigreaux column and condenser, nitrogen inlet, thermocouple, and stainless steel "C"-stirrer. The system was de-aerated with three vacuum-nitrogen purge cycles before the addition of acetic anhydride (2.5% molar excess). The flask was then heated in a fluidized sand bath while purging with nitrogen. The system was heated to 125° over 50 minutes, to 130° over 10 minutes, to 140° over 40 minutes, to 150° over 20 minutes, to 200° over 45 minutes, to 210° over 5 minutes, to 220° over 7 minutes, to 335° over 115 minutes, and to 340° over 10 minutes. After holding at this temperature for 10 minutes the system was slowly evacuated (in 100 mbar increments). The reading of the torque indicator was noted at the beginning of this vacuum period. Under vacuum at 340° C. the viscosity of the polymer increased as reflected by the reading on the torque indicator. When the increase in torque reached a predetermined level (delta torque, 35) the vacuum was released by purging nitrogen into the system. The system was taken down and the polymer was allowed to cool. The polymer plug was removed by breaking the flask, cut into pieces and then ground into small particles. The polymer had an IV (measured in 1:1 HFIP-PFP) of 6.9 dl/g and a melting temperature of 279.8° C. (by DSC). The melt viscosity of the polymer, measured on a Kayeness capillary rheometer at 300° C. (0.03" diameter X 1" length orifice) was 3145 poise at 100 sec-1 shear rate and 870 poise at 1000 sec-1 shear rate.

EXAMPLE 4: PREPARATION OF POLYMER CONTAINING 0.25 MOLE % OLIGOMERIC STABILIZER INCORPORATED INTO THE BACKBONE

4-Hydroxybenzoic acid (2.19 moles), 6-hydroxy-2-naphthoic acid (0.81 mole), poly(aminoterephthalic acid) (oligomeric stabilizer from Example 2 above, 0.0075 moles) and potassium acetate (0.06 mmole) were charged to a 1 liter 3-necked flask ("slim Jim") equipped with Vigreaux column and condenser, nitrogen inlet, thermocouple, and stainless steel "C"- stirrer. The system was de-aerated with three vacuum-nitrogen purge cycles before the addition of acetic anhydride (2.5% molar excess). The flask was then heated in a fluidized sand bath while purging with nitrogen. The system was heated to 125° over 50 minutes, to 130° over 10 minutes, to 140° over 40 minutes, to 150° over 20 minutes, to 200° over 45 minutes, to 210° over 5 minutes, to 220° over 7 minutes, to 335° over 115 minutes, and to 340° over 10 minutes. After holding at this temperature for 10 minutes the system was slowly evacuated (in 100 mbar increments). The reading of the torque indicator was noted at the beginning of this vacuum period. Under vacuum at 340° C. the viscosity of the polymer increased as reflected by the reading on the torque indicator. When the increase in torque reached a predetermined level (delta torque, 35) the vacuum was released (nitrogen was purged into the system). The system was taken down and the polymer was allowed to cool. The polymer plug was removed by breaking the flask, cut into pieces and then ground into small particles. The polymer had an IV (measured in 1:1 HFIP-PFP) of 6.5 dl/g and a melting temperature of 280.8° C. (by DSC). The melt viscosity of the polymer, measured on a Kayeness capillary rheometer at 300° C. (0.03" diameter X 1" length orifice) was 1765 poise at 100 sec-1 shear rate and 568 poise at 1000 sec-1 shear rate.

The above polymer presumably contains blocks of the benzoxazin-4-one units in the polymer backbone. Since these units arise by condensation of an orthoaminobenzoic acid function with another carboxylic acid function it might be possible to generate the same kinds of units through the condensation of aminoterephthalic acid with 4-hydroxybenzoic acid or 6-hydroxy-2-naphthoic acid units. This approach was attempted with the following polymer.

EXAMPLE 5: PREPARATION OF POLYMER CONTAINING 0.25 MOLE % AMINOTEREPHTHALIC ACID

4-Hydroxybenzoic (2.19 moles), 6-hydroxy-2-naphthoic acid (0.81 mole), aminoterephthalic Acid from Example 1 above (0.0075 moles), and potassium acetate (0.06 mmole) were charged to a 1 liter 3-necked flask ("slim Jim") equipped with Vigreaux column and condenser, nitrogen inlet, thermocouple, and stainless steel "C"- stirrer. The system was de-aerated with three vacuum-nitrogen purge cycles before the addition of acetic anhydride (2.5% molar excess). The flask was then heated in a fluidized sand bath while purging with nitrogen. The system was heated to 125° over 50 minutes, to 130° over 10 minutes, to 140° over 40 minutes, to 150° over 20 minutes, to 200° over 45 minutes, to 210° over 5 minutes, to 220° over 7 minutes, to 335° over 115 minutes, and to 340° over 10 minutes. After holding at this temperature for 10 minutes the system was slowly evacuated (in 100 mbar increments). The reading of the torque indicator was noted at the beginning of this vacuum period. Under vacuum at 340° C. the viscosity of the polymer increased as reflected by the reading on the torque indicator. When the increase in torque reached a predetermined level (delta torque, 35) the vacuum was released (nitrogen was purged into the system). The system was taken down and the polymer was allowed to cool. The polymer plug was removed by breaking the flask, cut into pieces and then ground into small particles. The polymer had an IV (measured in 1:1 HFIP-PFP) of 8.7 dl/g and a melting temperature of 290.8° C. (by DSC). The melt viscosity of the polymer, measured on a Kayeness capillary rheometer at 300° C. (0.03" diameter X 1" length orifice) was 6532 poise at 100 sec-1 shear rate and 1693 poise at 1000 sec-1 shear rate.

The IV, Tm, melt viscosity differences between the polymers prepared with poly(aminoterephthalic acid) and aminoterephthalic acid are large, demonstrating that they are clearly different materials.

EXAMPLE 6 (A COMPARATIVE EXAMPLE): BLENDED POLYMER CONTAINING THE NONOLIGOMERIC BENZOXAZIN-4-ONE STABILIZER OF FORMULA 7

The nonoligomeric stabilizer compound of Formula 7 (75 gm) was mixed with the CO 73/27 polymer (from Example 3, 4925 gm) which had been dried in a vacuum oven at 130° C. overnight. The mixture was then run through an extruder at 290° C. (barrel temperature) to produce a blend containing 1.5 wt% (0.55 mole %) of the stabilizer compound.

GENERAL PROCEDURE FOR SPINNING FIBERS FROM POLYMERS OF EXAMPLES 3–6

Ground samples of each of the polymers from Examples 3–6 were compressed into rods and placed in the heating block of a single filament fiber extruding machine. The melted samples were extruded through a single hole spinneret having diameter of 0.127 mm and a length of 0.178 mm while using a throughput rate of 0.45 gram/minute. The as-spun filaments were quenched in ambient air (72° F. and 65% relative humidity) prior to windup at a speed of 800 meters/minute. These filaments had a nominal cross-sectional density of 5 denier. Spinning temperatures, melt pressures and maximum take-up speeds are reported in Table I. Heat treatment of the fiber samples was done as follows.

GENERAL PROCEDURE FOR HEAT-TREATMENT OF THE SINGLE FILAMENT FIBER SAMPLES

Individual filaments from the above-described experiments were supported on racks and placed in an isothermal oven. Under a nitrogen atmosphere the fibers were heat-treated by holding at 230° C. for two hours, heating to 270° C. in one hour, and holding at this temperature for 16 hours.

GENERAL PROCEDURE FOR TENSILE TESTING OF FIBER SAMPLES

Heat-treated and as-spun fibers were subjected to tensile testing. Tensile strength, elongation, and tensile modulus were determined in accordance with ASTM D3822. The tensile properties of each of the samples (average of 10 breaks/sample) is reported in Table I.

WEATHERMOMETER TESTING OF FIBER SAMPLES TO CHECK UV STABILITY

As spun samples of fibers spun from each of the four polymers 3–6 were placed in a weatherometer and exposed to continuous irradiation by a Xenon lamp for 10 days. The xenon source was set at 0.35 W/n$^2$, and the weatherometer chamber was controlled at 60° C. black panel temperature and 30% relative humidity. Samples of each fiber were withdrawn from the weatherometer after 1, 2, 4, 7, and 10 days of irradiation. The tensile strength of each of these samples was determined in accordance with ASTM D3822, and they are reported in Tables II and III. The decrease in fiber strength as a function of exposure time serves as a measure of the UV-stability of the fiber. The data in Tables II and III have been plotted in FIGS. 1 and 2.

The data in Table I indicate that the polymer from Example 5 (aminoterephthalic acid polymerized into the polymer backbone) had to be spun at a higher temperature (344° vs 320° C.) than the others, generated a very high pack pressure, and gave the poorest fiber tenacity. Furthermore, it did not heat-treat well. The polymer from Example 4 (with the benzoxazin-4-one oligomeric stabilizer in the backbone) spun well, and gave good as-spun fiber properties. While the polymer from Example 4 heat-treated to a reasonable tenacity, the polymers from Example 5 and Example 6 (which contains the nonoligomeric stabilizer) did not. These results indicate the benefits derived from incorporating the oligomer into the polymer backbone as against incorporating a nonoligomer into the polymer backbone, as well as blending a nonoligomer with the polymer.

TABLE I

Spinning Parameters and Fiber Properties

| Polymer from Example | Spin Temp. (°C.) | Pack P$^4$ (psi) | As-Spun Ten$^1$. (gpd) | As-Spun Elong$^2$. (%) | As-Spun Mod$^3$. (gpd) | Heat-Treated Ten$^1$. (gpd) | Heat-Treated Elong$^2$. (%) | Heat-Treated Mod$^3$. (gpd) |
|---|---|---|---|---|---|---|---|---|
| 3 | 320 | 410 | 11.86 | 2.87 | 530 | 22.44 | 4.45 | 489 |
| 4 | 320 | 900 | 10.69 | 2.38 | 551 | 19.1 | 3.84 | 470 |
| 5 | 344 | 1950 | 8.63 | 2.34 | 454 | 11.3 | 2.98 | 402 |
| 6 | 320 | 700 | 11.32 | 2.8 | 538 | 13.6 | 2.96 | 475 |

$^1$Tensile strength in grams per denier.
$^2$Elongation.
$^3$Tensile modulus in grams per denier
$^4$Pressure

TABLE II

| Exposure, Days | Change in Tenacity with UV Exposure | | | |
|---|---|---|---|---|
| | Tenacity (gpd) for polymers from | | | |
| | Example 3 | Example 4 | Example 5 | Example 6 |
| 0 | 11.86 | 10.69 | 8.63 | 11.32 |
| 1 | 8.53 | 7.57 | 5.69 | 8.33 |
| 2 | 7.46 | 6.76 | 4.76 | 7.34 |
| 4 | 5.89 | 5.47 | 3.85 | 5.96 |
| 7 | 4.39 | 4.43 | 3.98 | 5.26 |
| 10 | 3.78 | 3.73 | 3.11 | 4.57 |

TABLE III

| Exposure, Days | Tenacity Retention (%) with UV Exposure | | | |
|---|---|---|---|---|
| | Tenacity Retention (%) for Polymers from | | | |
| | Example 3 | Example 4 | Example 5 | Example 6 |
| 0 | 100 | 100 | 100 | 100 |
| 1 | 71.9 | 70.8 | 65.9 | 73.6 |
| 2 | 62.9 | 63.2 | 55.2 | 64.8 |
| 4 | 49.7 | 51.2 | 44.6 | 52.7 |
| 7 | 37.0 | 41.4 | 46.1 | 46.5 |
| 10 | 31.9 | 34.9 | 36.0 | 40.4 |

I claim:

1. An oligomeric composition of matter which comprises, in its repeat units, suitable benzoxazin-4-one moieties that absorb ultraviolet radiation, and which has reactive functionalities through which said oligomeric composition is incorporated by chemical bonding into the backbone of a polyester to offer stability to said polyester against ultraviolet radiation, wherein said repeat units number 2-200, and wherein said oligomeric composition has sufficient thermal stability to withstand processing temperatures of about 300°-350° C.

2. The oligomeric composition of claim 1, wherein said processing temperatures are about 200°-300° C.

3. The oligomeric composition of claim 1, wherein said polyester is a liquid crystal polyester.

4. The oligomeric composition of claim 1, wherein said benzoxazin-4-one functionality is of the formula:

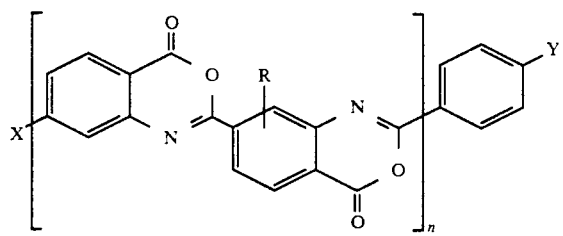

wherein R=H, an alkyl group containing up to about 12 carbons, a cycloalkyl containing up to about 8 carbons, an alkoxy group containing up to about 8 carbons, a halide, or an aryl group containing up to about 10 carbons, X and Y are same or different and are selected from the group consisting of $HN_2$, HNR, COOH, and OH, with R referring to the same alkyl, cycloalkyl and aryl groups described above.

5. A composition which comprises a polyester, and a functionality which is chemically bonded into the backbone of said polyester, which functionality contains 2-100 repeat units of moieties that can absorb ultraviolet radiation, wherein said composition can be thermally processed at about 300°-350° C. into articles with said functionality being present in said articles with no chemical change.

6. The composition of claim 5, wherein said thermal processing comprises spinning of said polyester into fiber followed by heat treating said fiber.

7. The composition of claim 5, wherein said functionality is present in the range of about 0.1-10 weight percent based on said polyester.

8. The composition of claim 5, wherein said functionality is present in the range of about 0.5-3 weight percent based on said polyester.

9. An oligomeric composition of matter which comprises 2-200 repeat units of benzoxazin-4-one moieties that absorb ultraviolet radiation, which composition can be blended with a polyester to offer stability to said polyester against ultraviolet radiation, and which composition retains its chemical integrity when said blended polyester is processed at temperatures of about 300°-350° C.

10. A method of stabilizing a polyester against ultraviolet radiation comprising incorporating into said polyester a functionality of repeat units which comprises, in said repeat units, benzoxazin-4-one moieties that absorb the ultraviolet radiation, wherein said repeat units number 2-200, and wherein said stabilized polyester is further processed into articles at temperatures of about 300°-350° C., and said functionality retains its structural functionality retains its structural integrity at said processing temperatures.

11. An article stabilized against ultraviolet radiation and obtained from thermal processing of a polyester composition at temperatures of about 300°-350° C., wherein said polyester composition comprises, in its repeat units, a functionality of repeat units which functionality possesses sufficient thermal stability to withstand said processing temperatures, and which comprises a benzoxazin-4-one moiety in said repeat units, with said repeat units numbering 2-200.

* * * * *